(12) United States Patent
Hill et al.

(10) Patent No.: US 9,173,767 B2
(45) Date of Patent: Nov. 3, 2015

(54) THIN CONDOM

(75) Inventors: David Michael Hill, Bishops Stortford (GB); Christophe Brodin, Cambridge (GB)

(73) Assignee: LRC PRODUCTS LIMITED, London (GB)

( * ) Notice: Subject to any disclaimer, the term of this patent is extended or adjusted under 35 U.S.C. 154(b) by 1378 days.

(21) Appl. No.: 12/520,286

(22) PCT Filed: Dec. 20, 2007

(86) PCT No.: PCT/GB2007/004914
§ 371 (c)(1),
(2), (4) Date: Aug. 21, 2009

(87) PCT Pub. No.: WO2008/075067
PCT Pub. Date: Jun. 26, 2008

(65) Prior Publication Data
US 2010/0229873 A1    Sep. 16, 2010

(30) Foreign Application Priority Data

Dec. 21, 2006 (GB) .................... 0625551.7

(51) Int. Cl.
*A61F 6/04*    (2006.01)
*A61L 31/04*   (2006.01)

(52) U.S. Cl.
CPC ........ *A61F 6/04* (2013.01); *A61L 31/041* (2013.01)

(58) Field of Classification Search
USPC .............................. 128/844; 428/423.4, 423.9
See application file for complete search history.

(56) References Cited

U.S. PATENT DOCUMENTS

| 4,100,309 A | 7/1978 | Micklus et al. |
| 4,963,623 A * | 10/1990 | Miller et al. ............... 525/237 |
| 5,195,537 A * | 3/1993 | Tillotson ..................... 128/844 |
| 2004/0002729 A1* | 1/2004 | Zamore ....................... 606/194 |
| 2005/0103349 A1* | 5/2005 | Couvreur .................... 128/844 |

OTHER PUBLICATIONS

PCT International Preliminary Report on Patentability, PCT/GB2007/004914, Dec. 20, 2007.

* cited by examiner

*Primary Examiner* — Victoria J Hicks
*Assistant Examiner* — Kari Petrik
(74) *Attorney, Agent, or Firm* — Troutman Sanders LLP; Ryan A. Schneider; Troy S. Kleckley

(57) ABSTRACT

A condom comprises natural rubber and polyurethane. Preferably, the condom has a single wall thickness of less than 55 µm. More preferably the condom has a single wall thickness of less than 55 µm and a burst pressure of 1.0 kPa or above. A process for making the condom comprises mixing polyurethane and natural rubber latex and forming a condom therefrom.

11 Claims, 4 Drawing Sheets

Effect of X-SBR loading in NRL on burst and tensile properties

| X-SBR Loading (pphr) | Condom thickness (µm) | Burst volume (dm³) | Burst pressure (kPa) | Tensile strength (MPa) | Elongation-at-break (%) |
|---|---|---|---|---|---|
| 1 | 65 | 35 | 1.6 | 35 | 880 |
| 1 | 54 | 32 | 1.3 | 31 | 854 |
| 1 | 43 | 32 | 1.0 | 32 | 882 |
| 2 | 69 | 35 | 1.8 | 35 | 865 |
| 2 | 56 | 31 | 1.4 | 31 | 853 |
| 2 | 46 | 33 | 1.1 | 31 | 878 |
| 4 | 68 | 31 | 2.0 | 33 | 836 |
| 4 | 58 | 29 | 1.7 | 34 | 844 |
| 4 | 45 | 28 | 1.1 | 32 | 848 |
| 5 | 69 | 34 | 1.9 | 35 | 890 |
| 5 | 64 | 31 | 1.6 | 37 | 880 |
| 5 | 54 | 29 | 1.3 | 34 | 880 |
| 10 | 55 | 19 | 1.4 | 33 | 890 |
| 10 | 54 | 22 | 1.5 | 28 | 830 |
| 10 | 54 | 22 | 1.6 | 28 | 825 |

Where:   X-SBR = Litex® S21C, PolymerLatex GmbH
pphr = parts per hundred rubber
condom thickness = single-wall thickness measured at mid-body

Figure 1

Effect of X-SBR loading in NRL on burst and tensile properties

| X-SBR Loading (pphr) | Condom thickness (μm) | Burst volume (dm$^3$) | Burst pressure (kPa) | Tensile strength (MPa) | Elongation-at-break (%) |
|---|---|---|---|---|---|
| 1 | 65 | 35 | 1.6 | 35 | 880 |
| 1 | 54 | 32 | 1.3 | 31 | 854 |
| 1 | 43 | 32 | 1.0 | 32 | 882 |
| 2 | 69 | 35 | 1.8 | 35 | 865 |
| 2 | 56 | 31 | 1.4 | 31 | 853 |
| 2 | 46 | 33 | 1.1 | 31 | 878 |
| 4 | 68 | 31 | 2.0 | 33 | 836 |
| 4 | 58 | 29 | 1.7 | 34 | 844 |
| 4 | 45 | 28 | 1.1 | 32 | 848 |
| 5 | 69 | 34 | 1.9 | 35 | 890 |
| 5 | 64 | 31 | 1.6 | 37 | 880 |
| 5 | 54 | 29 | 1.3 | 34 | 880 |
| 10 | 55 | 19 | 1.4 | 33 | 890 |
| 10 | 54 | 22 | 1.5 | 28 | 830 |
| 10 | 54 | 22 | 1.6 | 28 | 825 |

Where: X-SBR = Litex® S21C, PolymerLatex GmbH
pphr = parts per hundred rubber
condom thickness = single-wall thickness measured at mid-body

Figure 2

Effect of NRL condom wall-thickness on burst and tensile properties

| Condom thickness (μm) | Burst volume (dm³) | Burst pressure (kPa) | Tensile strength (MPa) | Elongation-at-break (%) |
|---|---|---|---|---|
| 65 | 55 | 1.8 | 31 | 900 |
| 55 | 45 | 1.3 | 32 | 895 |
| 56 | 51 | 1.4 | 28 | 895 |
| 47 | 47 | 1.4 | 31 | 925 |
| 47 | 41 | 1.0 | 30 | 920 |
| 46 | 48 | 1.1 | 30 | 895 |

Where: pphr = parts per hundred rubber
condom thickness = single-wall thickness measured at mid-body

Figure 3

Effect of PUL loading in NRL on burst and tensile properties

| PUL loading (pphr) | Condom thickness (μm) | Burst volume (dm³) | Burst pressure (kPa) | Tensile strength (MPa) | Elongation-at-break (%) |
|---|---|---|---|---|---|
| 5 | 69 | 47 | 1.9 | 31 | 900 |
| 5 | 69 | 46 | 1.7 | 32 | 905 |
| 5 | 66 | 46 | 2.0 | 25 | 824 |
| 5 | 59 | 47 | 1.6 | 35 | 920 |
| 5 | 56 | 44 | 1.5 | 33 | 900 |
| 5 | 55 | 43 | 1.6 | 27 | 835 |
| 5 | 47 | 42 | 1.3 | 27 | 850 |
| 10 | 62 | 43 | 2.0 | 25 | 832 |
| 10 | 57 | 42 | 1.6 | 29 | 845 |
| 10 | 56 | 40 | 1.7 | 31 | 890 |
| 10 | 55 | 38 | 1.6 | 22 | 766 |
| 10 | 46 | 37 | 1.4 | 24 | 820 |
| 15 | 66 | 40 | 2.2 | 19 | 738 |
| 15 | 58 | 36 | 1.9 | 19 | 734 |
| 15 | 47 | 35 | 1.5 | 20 | 754 |
| 20 | 44 | 31 | 1.5 | 22 | 769 |
| 20 | 44 | 26 | 1.4 | 22 | 751 |
| 20 | 41 | 29 | 1.3 | 22 | 768 |
| Incorez® W385/092 | | | | | |
| 7.5 | 44 | 35 | 1.4 | 25 | 796 |

Where: PUL = Acralen® U900, PolymerLatex GmbH
pphr = parts per hundred rubber
condom thickness = single-wall thickness measured at mid-body The data are taken from Figure 1 (NRL/X-SBR), Figure 2 (NRL) and Figure 3 (NRL/PUL)
The least square fits for the NRL and NRL/X-SBR data overlap and only begin to diverge
at low thickness/burst pressure values

THIN CONDOM

CROSS-REFERENCE TO RELATED APPLICATIONS

This application is a US National Stage of International Application No. PCT/GB07/04914, filed 20 Dec. 2007, which claims the benefit of GB 0625551.7, filed 21 Dec. 2006.

FIELD OF THE INVENTION

The present invention relates to condoms comprising natural rubber and polyurethane, particularly thin-walled condoms, and a method for making them.

BACKGROUND OF THE INVENTION

The majority of condoms are made from natural rubber latex (NRL) by well known manufacturing processes. To ensure that condoms are suitable for use, their properties must meet the requirements of national, regional or international standards, which normally include a minimum burst pressure requirement.

While condom wall thickness is normally fairly low, being between 50 μm and 70 μm, it would be beneficial to reduce this even further to encourage the use of condoms. A perceived loss of sensitivity when using a condom is often used as an excuse for not using them, leading to an increased risk of pregnancy or sexually transmitted infections. Accordingly, it would be desirable to be able to manufacture thinner condoms. Not only is it desirable to make thinner condoms, these thin condoms must also meet the burst pressure requirements of the standards.

Although attempts have been made to make thinner condoms, it has not heretofore been possible to make thin condoms which meet the requirements for burst pressure specified in the standards.

The thinness of the condom is typically determined by the single wall thickness.

Single-wall thickness measurement on a condom is done via a weight measurement. A 20 mm ring section is cut from a parallel-sided part of the condom, preferably at the mid-body of the condom (such 'ring' sample pieces are typically used for tensile testing, and the thickness measurements are used in calculation of tensile strength). Knowing the circumference of the ring, its length of height and the density of the latex film, single-wall thickness can be calculated using the equation:

$$\text{Single-wall thickness} = \frac{\text{Weight}}{\text{Density} \times \text{circumference} \times \text{height} \times 10{,}000}$$

Where

Single-wall thickness=thickness of one condom wall (μm)

Density=density of condom film (g/cm$^2$)

Circumference=circumference of ring sample (cm)

Height=height of ring sample (cm)

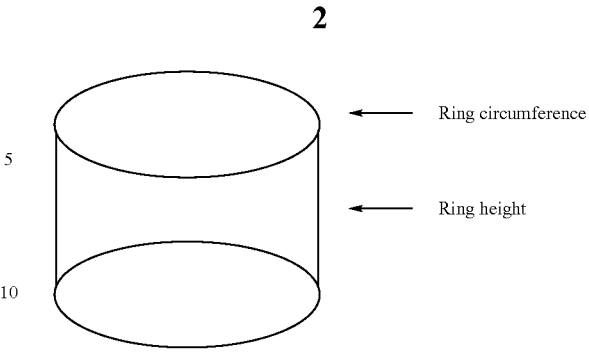

Ring circumference

Ring height

The international condom standard (*BS EN ISO* 4074:2002 *Natural latex rubber condoms: Requirements and test methods*), along with many other standards, includes a requirement that condoms have a minimum burst pressure of 1.0 kPa when tested according to the method in the standard. In brief, the test requires that a condom is inflated at a fixed rate of flow of air, whilst both the pressure and volume of air in the condom are continuously monitored so that the pressure and volume readings when the condom fails by bursting are recorded. These measurements are known, respectively, as the burst pressure (measured in kilopascals, kPa) and burst volume (measured in liters, L, or decimeters cubed, dm$^3$). This testing is carried out on a number of condoms from each batch, the number being determined by the batch size.

As the wall of the condom is made thinner, the pressure required to inflate and eventually burst the condom decreases. As a result, there is a lower limit to the condom wall thickness that can comply with the burst pressure requirements of the standard. Furthermore, inflation volume and inflation pressure are linked. Apart from the initial stages of inflation, the larger the inflation volume, the larger the inflation pressure for any condom type. Modulus is essentially a measure of stiffness, such that a lower modulus material is more pliable or elastic. Increasing the modulus (i.e. increasing the stiffness) of the condom material also increases the burst pressure when compared to a condom made from a material with a lower modulus, at the same inflation volume. That is, the higher the modulus of the condom material, the higher the pressure necessary to burst the condom, at a given inflation volume. However, in almost all cases, increasing the condom modulus has the additional effect of reducing the burst volume. Because burst pressure is related to burst volume, any reduction in burst volume will also lead to a reduced burst pressure. Thus, a condom made from a latex formulation that results in a lower burst volume will also have a lower burst pressure.

Previous attempts to produce a very thin condom complying with the burst pressure requirements have failed because use of materials with a higher modulus, in an attempt to maintain minimum burst pressures that comply with the required standards at low condom wall thickness, almost invariably causes reduced burst volume, which results in reduced burst pressure.

Two approaches have been tried in the past to achieve thinner condoms. Firstly, attempts have been made to make condoms from natural rubber latex (NRL) but using less NRL to give thinner condom walls. Secondly, attempts have been made to make condoms from synthetic materials having higher tensile properties than NRL.

In the first approach (using less NRL), there is a limit to how thin the condom walls can be before the condoms start failing to meet the requirements of the standards, and attempts to alter process parameters to alleviate this problem have been unsuccessful. It has been found that, in order to ensure that the manufacturing batch pass rate is as high as possible, the mean burst pressure of each batch typically needs to be at least two standard deviations above the minimum requirements given in the standards. This has been found to result in a minimum NRL condom thickness of between about 50 μm and about 55 μm (single wall thickness).

Using the second approach (using synthetic materials with superior tensile strength to NRL), it has been possible to make thin condoms. However, the synthetic materials used also tend to have higher low strain moduli and lower elongation-at-break than NRL and so the benefits of having a thinner condom, such as improved perceived sensitivity, are negated by these thinner synthetic condoms being perceived as being stiffer and less flexible, which is undesirable. As a result, these condoms made from synthetic materials are unsatisfactory.

Recent work with high-styrene styrene-butadiene rubber latex (SBR) and carboxylated SBR (X-SBR) gave reinforcement of tensile modulus but we have found that condoms made from NRL incorporating SBR and/or X-SBR suffer from the lower burst volumes described above. As a result, thin condoms made from NRL and SBR/X-SBR blends are not predicted to meet the burst pressure requirements of the standards.

The data shown in FIGS. 1 and 2 illustrate that although tensile strength is increased for X-SBR/NRL blends (FIG. 1) compared to NRL alone (FIG. 2), the addition of X-SBR has lowered the burst volume and, as a consequence, the burst pressure for condoms made from X-SBR/NRL blends (FIG. 1) is similar to that of the unmodified formulation (that is, without the addition of X-SBR (FIG. 2)) at similar condom thicknesses.

We have now found that it is possible to make NRL condoms that are significantly thinner than current NRL condoms and which have acceptable overall properties, such as, in particular, perceived stiffness, and meet the requirements of the standards, by blending a polyurethane latex with natural rubber latex.

The limitations described above, where reinforcement leads to higher modulus, lower burst volumes but no improvement in burst pressure have, surprisingly, been overcome by using polyurethane as a reinforcing blend with natural rubber in the manufacture of condoms.

BRIEF SUMMARY OF THE INVENTION

According to the present invention in its broadest aspect, there is provided a condom comprising natural rubber and polyurethane. Natural rubber and polyurethane are preferably present as a blend in condoms according to the invention. Ideally, a homogenous blend or mixture is used.

Condoms according to the invention can be made from a latex which comprises a blend of natural rubber latex and polyurethane latex.

In a preferred aspect, there is provided a condom comprising natural rubber and polyurethane, and having a single wall thickness of less than about 55 μm and a burst pressure of 1.0 kPa or above.

Preferably, the single wall thickness is about 50 μm or less and the burst pressure is about 1.2 kPa or above. The burst pressure is as defined by BS EN ISO 4074:2002.

In another aspect, the invention provides the use of polyurethane in the manufacture of a thin natural rubber latex condom. Typically, the polyurethane is used in the form of a dispersion. Preferably, the polyurethane is used in the manufacture of natural rubber latex condoms having a single wall thickness of less than about 55 μm, more preferably of 50 μm or less.

According to the present invention there is also provided a process for making a condom which process comprises mixing polyurethane and natural rubber latex and forming a condom therefrom. Preferably, the polyurethane is used as a dispersion. For example, a blend of a polyurethane dispersion and natural rubber latex is used. Preferably, a polyurethane latex (PUL) is used as a reinforcing blend with NRL in the manufacture of condoms. Preferably, the polyurethane is a polyurethane latex. Most preferably, the process comprises mixing polyurethane latex and natural rubber latex to form a blend, and forming a condom therefrom.

DESCRIPTION OF THE FIGURES

FIG. 1 shows the effect of carboxylated styrene butadiene rubber (X-SBR) loading on the burst and tensile properties of natural rubber latex/X-SBR condoms.

FIG. 2 shows the effect of single wall thickness on the burst and tensile properties of unmodified natural rubber latex condoms.

FIG. 3 shows the effect of polyurethane (PUL) loading in natural rubber latex on the burst and tensile properties of condoms made from a natural rubber/polyurethane blend.

DETAILED DESCRIPTION OF PREFERRED EMBODIMENTS

Figure 4:
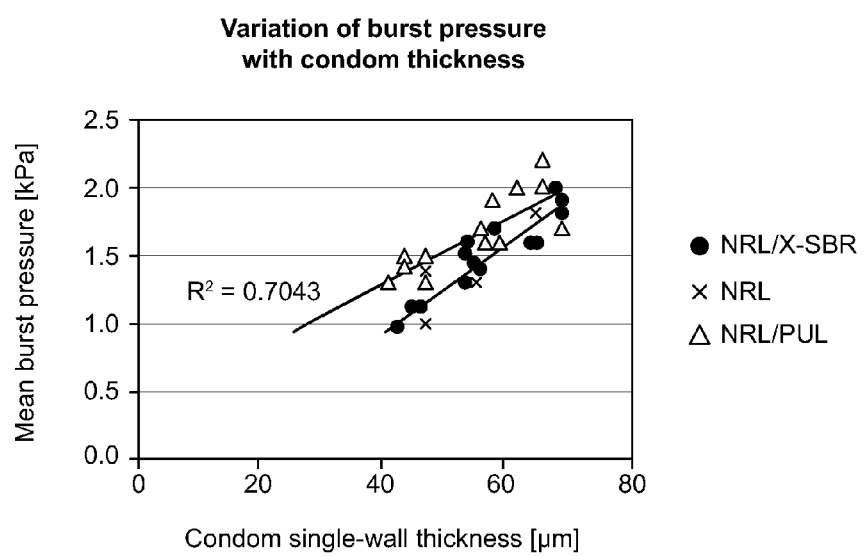
FIG. 4 is a graph showing the variation of burst pressure with condom thickness for natural rubber latex (NRL) condoms, natural rubber/carboxylated-styrene rubber butadiene (NRL/X-SBR) rubber condoms and natural rubber/polyurethane (NRL/PUL) blend condoms.

The terms polyurethane latex and polyurethane dispersions are used interchangeably. As used herein, therefore, the term 'polyurethane dispersion' includes polyurethane latexes.

A significant improvement in burst pressure is obtained through the use of NRL/PUL blends. We have found that addition of polyurethane (PUL) to NRL does not reduce the burst volume to the same extent as addition of X-SBR. As a result, condoms made from a PUL reinforced blend with NRL have higher burst pressures than NRL/X-SBR blends.

We have found that condoms made from a natural rubber/polyurethane blend are superior to natural rubber latex condoms. For example, we have found that natural rubber/polyurethane blend condoms have a consistently higher mean burst pressure than natural rubber latex condoms, even at single wall thicknesses approaching 40 μm (FIG. 4).

Condoms with a single wall thickness of 55 μm or less are preferred. Preferably, condoms according to the invention have a single wall thickness of less than 55 μm, such as, for example, 35 to 55 μm, more preferably 40 to 50 μm, even more preferably a single wall thickness of about 40 μm or less.

Condoms with a burst pressure of greater than 1.0 kPa, preferably greater than 1.1 kPa, more preferably greater than 1.2 kPa are preferred. Advantageously, the condoms have a mean burst pressure of at least two standard deviations above the minimum requirement given in the standards. For example, condoms having a mean burst pressure of at least two standard deviations above the 1.0 kPa minimum burst pressure requirement of the international standard BS EN ISO 4074:2002 are preferred. We prefer to have a mean burst pressure of about 1.2 kPa or higher, to ensure the condoms will be capable of passing the international standard's burst pressure requirements on a consistent basis. It is highly preferred that these burst pressures are achieved in condoms having a single wall thickness of 35 µm to 55 µm or less, preferably 40 µm to 50 µm. Higher burst pressures, for example 1.3 kPa or above, or 1.4 kPa or above, or 1.5 kPa or above are also achievable for condoms thinner than about 50 µm, depending upon the blend.

At polyurethane levels of 15 or 20 parts per hundred rubber (pphr), the burst pressure is such that condoms are predicted to meet the requirements of BS EN ISO 4074:2002 at a thickness of as low as 40 µm or lower. This represents a significant improvement on the thicknesses that can be achieved with unblended NRL formulations, which have a lower thickness limit of about 50 to 55 µm.

We have conducted trials on a range of formulations containing different levels of polyurethane, and the properties of condoms made from these formulations are summarised in FIG. 3 and shown graphically in FIG. 4. It is apparent from FIG. 4 that natural rubber/polyurethane blend condoms have a higher burst pressure than both natural rubber latex condoms and natural rubber/X-SBR condoms at all loading levels of polyurethane tested.

Any suitable polyurethane may be used. Preferably, the polyurethane is an aliphatic polyurethane. However, aromatic polyurethanes may be used. Preferred polyurethanes for use in processes according to the invention include anionically or non-ionically-stabilised aliphatic polyurethanes, including anionically or non-ionically-stabilised aliphatic polyurethane latexes. Preferred aliphatic polyurethanes include, but are not limited to, aliphatic polycarbonate polyurethanes, and aliphatic polyester polyurethanes. Preferably, the latex is substantially solvent-free, or contains low levels of solvent. Most preferably, the latex is free from the co-solvent N-methylpyrrolidone. The latex may also, or alternatively, be substantially free from emulsifier.

A preferred aliphatic polycarbonate polyurethane latex for use according to the invention is Acralen® U-900, which is commercially available from PolymerLatex GmbH, Germany. Any suitable aliphatic polyester polyurethane latex can be used.

Another preferred polyurethane latex for use according to the invention is Incorez W835/092, which is commercially available from Industrial Copolymers Ltd, UK.

Incorez W835/092 is an aliphatic polycarbonate polyurethane latex. However, any suitable aliphatic polycarbonate polyurethane latex can be used.

Any suitable amount of polyurethane can be used in the condoms of the invention. We prefer condoms comprising a natural rubber/polyurethane blend formulation comprising polyurethane in an amount from 1 pphr to 50 pphr (measured as dry weight). More preferably, condoms comprise polyurethane in an amount from 5 pphr to 20 pphr. Suitable amounts of polyurethane depends on the type of polyurethane. For example, for aliphatic polyurethane latexes, we prefer condoms comprising polyurethane in an amount from 1 pphr to 50 pphr (dry weight), more preferably from 5 pphr to 20 pphr. Where an aliphatic polyester polyurethane, such as for example Acralen® U-900, is used, we prefer condoms comprising a natural rubber/polyurethane blend comprising the aliphatic polyester polyurethane in an amount from 5 pphr to 20 pphr, more preferably from 12 pphr to 18 pphr. Alternatively, where an aliphatic polycarbonate polyurethane such as, for example, Incorez W835/092 is used, we prefer condoms comprising a natural rubber/polyurethane blend comprising the aliphatic polycarbonate polyurethane, for example Incorez W835/092, in an amount of from 5 to 10 pphr, more preferably 5 pphr to 7.5 pphr.

In a preferred embodiment, condoms are made from a latex blend formulation comprising the following ingredients:

| Ingredient function | Range (pphr) |
|---|---|
| Natural Rubber Latex | 100 |
| Stabilisers | 0.40-0.80 |
| Vulcanising agent | 0.45-0.75 |
| pH adjuster | 0.05-0.10 |
| Vulcanisation activator | 0.40-0.75 |
| Accelerator | 0.40-0.75 |
| Antioxidant | 0.15-0.25 |
| Polyurethane latex | 5-20 |
| Ammoniated water | 25-33 |

The present invention also provides a process for making a condom which process comprises mixing polyurethane latex and natural rubber latex to form a blend, and forming a condom therefrom.

The condom can be formed in any suitable way. Typically, this is done by dipping a condom-shaped former into the blend to form a film which is subsequently dried and cured, as will be clear to those in the art.

We prefer to add the polyurethane latex to compounded, prevulcanised natural rubber latex. Preferably, the polyurethane latex is added to the natural rubber latex before transfer to the dipping plant. In a preferred embodiment, the process comprises the following steps:

1. Prevulcanisation: add compounding ingredients to the latex and prevulcanise at an elevated temperature until the appropriate swelling index is reached.
2. Maturation: cool to ambient temperature and add further vulcanising agent as appropriate, and allow the latex to mature at ambient temperature until the appropriate swelling index is reached.
3. Final stage compounding: add more vulcanising agent as appropriate and heat at moderate temperature until the appropriate swelling index is reached. Conventional crosslink density measurement typically requires a disc of a specified diameter to be cut from the latex film. This is then placed in a solvent such as toluene or n-heptane, which causes the film to swell; the diameter of the disc is measured when the swelling equilibrates, and the final and initial diameters are used to calculate a "swelling index".
4. Final adjustment: add polyurethane to the fully compounded latex, mix and dilute if necessary to correct dipping viscosity; add to dipping plant.

We prefer to make latex films by "straight dipping", that is where no coagulation of the latex is used (by dipping into coagulant before the latex dipping).

Preferably, condoms made by the process according to the invention have a single wall thickness of 55 µm or less, preferably 35 µm to 55 µm or less, more preferably 40 µm to 50 µm.

Any suitable polyurethane can be used. Preferred polyurethanes for use in the method according to the invention are anionically or non-ionically stabilised aliphatic polyurethane latexes. Advantageously, these latexes comprise low levels of solvent, or are solvent-free. Preferably, these latexes are free from N-methylpyrrol-idone. Aromatic polyurethane latexes can also be used in the method provided by the present invention.

We prefer to add a polyurethane in an amount from 1 to 50 pphr, preferably an amount from 5 to 20 pphr. Where the polyurethane comprises an aliphatic polyester polyurethane, such as Acralen® U-900 for example, it is preferably added in an amount from 12 to 18 pphr. Alternatively, a preferred polyurethane comprises an aliphatic polycarbonate polyurethane, for example Incorez W835/092. Where condoms made by the process according to the invention comprise a polyurethane which comprises an aliphatic polycarbonate polyurethane, it is preferably added in an amount from 5 to 10 pphr, more preferably 5 pphr to 7.5 pphr.

The invention claimed is:

1. A condom consisting of:
natural rubber latex in an amount of 100 pphr;
a stabilizer in an amount from 0.40 pphr to 0.80 pphr;
a vulcanizing agent in an amount from 0.45 pphr to 0.75 pphr;
a pH adjuster in an amount from 0.05 pphr to 0.10 pphr;
a vulcanizing activator in an amount from 0.40 pphr to 0.75 pphr;
an accelerator in an amount from 0.40 pphr to 0.75 pphr;
an antioxidant in an amount from 0.15 pphr to 0.25 pphr;
a polyurethane latex in an amount from 5 pphr to 20 pphr; and
ammoniated water in an amount from 25 pphr to 33 pphr;
wherein the polyurethane latex comprises an aliphatic polyurethane;
wherein the condom has a single wall thickness of less than 55 um and a burst pressure of 1.0 kPa or above, further wherein the single wall thickness is calculated using the equation:

$$\text{Single wall thickness} = \frac{\text{Weight}}{\text{Density} \times \text{circumference} \times \text{height} \times 10{,}000}$$

wherein single wall thickness=thickness of one condom wall (um), density=density of condom film (g/cm$^2$), circumference=circumference of ring sample (cm), and height=height of ring sample (cm).

2. The condom according to claim 1, wherein the natural rubber and the aliphatic polyurethane are present as a blend.

3. The condom according to claim 1, wherein the single wall thickness is less than 50 μm.

4. The condom according to claim 1, wherein the condom has a burst pressure of 1.2 kPa or above.

5. The condom according to claim 1, wherein the condom comprises the aliphatic polyurethane in an amount from 5 pphr to 20 pphr (dry weight).

6. The condom according to claim 1, wherein the aliphatic polyurethane comprises an aliphatic polyester polyurethane.

7. The condom according to claim 6, wherein the condom comprises the aliphatic polyester polyurethane in an amount from 10 pphr to 20 pphr (dry weight).

8. The condom according to claim 7, wherein the condom comprises the aliphatic polyester polyurethane in an amount from 12 pphr to 18 pphr (dry weight).

9. The condom according to claim 1, wherein the aliphatic polyurethane comprises an aliphatic polycarbonate polyurethane.

10. The condom according to claim 9, wherein the condom comprises the aliphatic polycarbonate polyurethane in an amount from 5 pphr to 10 pphr (dry weight).

11. The condom according to claim 9, wherein the condom comprises the aliphatic polycarbonate polyurethane in an amount from 5 pphr to 7.5 pphr (dry weight).

* * * * *